(12) United States Patent
Honold et al.

(10) Patent No.: US 7,169,781 B2
(45) Date of Patent: Jan. 30, 2007

(54) IMIDAZOLE DERIVATIVES AND THEIR USE AS PHARMACEUTICAL AGENTS

(75) Inventors: Konrad Honold, Penzberg (DE); Stefan Scheiblich, Penzberg (DE); Thomas von Hirschheydt, Penzberg (DE); Edgar Voss, Bichl (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 112 days.

(21) Appl. No.: 10/961,907

(22) Filed: Oct. 12, 2004

(65) Prior Publication Data

US 2005/0113342 A1    May 26, 2005

(30) Foreign Application Priority Data

Oct. 17, 2003    (EP) .................... 03023677

(51) Int. Cl.
  *C07D 403/04*    (2006.01)
  *A61K 31/4178*    (2006.01)
  *C07D 239/38*    (2006.01)
(52) U.S. Cl. ............... 514/235.8; 514/275; 544/122; 544/331
(58) Field of Classification Search ............. 544/122, 544/331; 514/235.8, 275
  See application file for complete search history.

(56) References Cited

U.S. PATENT DOCUMENTS 5,656,644 A    8/1997 Adams et al.
6,610,695 B1    8/2003 Adams et al.

FOREIGN PATENT DOCUMENTS

WO    WO 96/18626    6/1996
WO    WO 03/087026    10/2003

OTHER PUBLICATIONS

Herynk et al., Medline Abstract (Cancer Research, vol. 63, Issue 11, pp. 2990-2996) Jun. 2003.*
Simone, Oncoloy: Introduction, Cecil Textbook of Medicine, 20th Edition, vol. 1, pp. 1004-1010, 1996.*
Traxler, Protein Tyrosine Kinase Inhibitors in cancer treatment, Exp. Opin. Ther. Patents, 7(6):571-588, 1997.*
Von Hirschheydt et al., Synthesis, 12, pp. 2062-2065 (2004).

* cited by examiner

*Primary Examiner*—Deepak Rao
(74) *Attorney, Agent, or Firm*—George W. Johnston; Patricia S. Rocha-Tramaloni; Brian C. Remy

(57) ABSTRACT

Compounds of the general formula (I)

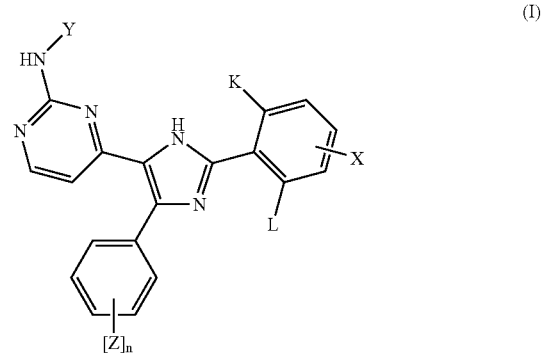

are presented which arevaluable therapeutics for the treatment of cancer and cancer related diseases.

12 Claims, No Drawings

IMIDAZOLE DERIVATIVES AND THEIR USE AS PHARMACEUTICAL AGENTS

BACKGROUND OF THE INVENTION

This invention relates to new imidazole derivatives and their pharmaceutically acceptable salts. The compounds are protein-tyrosine kinase inhibitors, especially inhibitors of c-met and src kinases and are therefore excellent therapeutics for the treatment of cancer. The invention also relates to pharmaceutical compositions which contain these new compounds as active agents for the treatment of cancer and cancer related diseases.

WO 96/18626 describes inhibitors of tyrosine kinases and c-met kinase which are derivatives of 2-(2,6-dichlorophenyl)-4-phenyl-5-(pyridin-4yl)-1H-imidazole (examples 5, 6 and 55). However they show unfavorable cytochrome P450 interactions.

It has now been found that the compounds according to this invention avoid this disadvantage and are potent inhibitors of c-met kinase and src family tyrosine kinase with good solubility.

SUMMARY OF THE INVENTION

The present invention therefore relates to new compounds of the general formula (I)

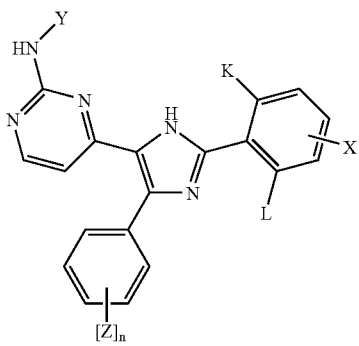

(I)

wherein K, L, X, Y and Z are defined herein.

The compounds according to this invention show activity as protein kinase inhibitors, in particular c-met kinase and src family tyrosine kinase inhibitors, and may therefore be useful for the treatment of diseases mediated by said tyrosine kinases. The family of tyrosine kinases plays an important role in the regulation of cell signaling and cell proliferation by phosphorylating tyrosine residues of peptides and proteins. Inappropriate activation of tyrosine kinases is known to be involved in a variety of disease states including inflammatory, immunological, CNS disorders, or oncological disorders, or bone diseases. See for example Susva, M., et al., Trends Pharmacol. Sci. 21 (2000) 489–495; Biscardi, J. S., et al., Adv. Cancer Res. 76 (2000) 61–119.

C-met mutations have been well-described in hereditary and sporadic human papillary renal carcinomas and have been reported in ovarian cancer, childhood hepatocellular carcinoma, metastatic head and neck squamous cell carcinomas, and gastric cancer. C-met is also over-expressed in both non-small cell lung cancer and small cell lung cancer cells, in breast, colon and prostate tumors. Since c-met appears to play an important role in oncogenesis of a variety of tumors, various inhibition strategies have been employed to therapeutically target this receptor tyrosine kinase.

The usefulness of inhibiting the protein-tyrosine kinase c-met for inhibiting tumor growth and invasion has been shown in many well documented preclinical experiments (e.g.: Abounader, R., et al., J. Natl. Cancer Inst. 91 (1999) 1548–1556; Laterra, J., et al., Lab. Invest. 76 (1997) 565–577; Tomioka, D., Cancer Res. 61 (2001) 7518–7524; Wang, R., et al., J. Cell Biol. 153 (2001) 1023–1033).

DETAILED DESCRIPTION OF THE INVENTION

The present invention relates to new compounds of the general formula

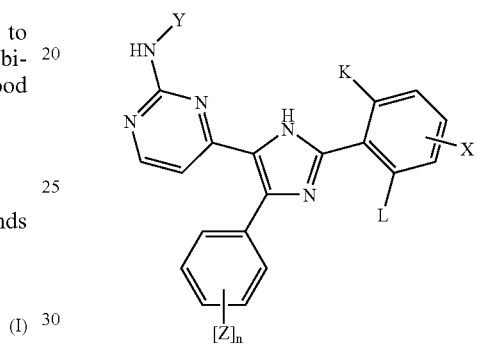

I wherein

K,L independently represent hydrogen; halogen; alkyl; —OH; or —O-alkyl;

X is hydrogen; —OR$^1$; —SR$^2$; —S(O)R$^2$; —S(O)$_2$R$^2$; —CH$_2$—S—CH$_2$—C(O)$_2$—CH$_2$—CH$_3$; —CH$_2$—S—(CH$_2$)$_2$—OH or a group A$^1$-Q; wherein A$^1$ represents a C$_1$–C$_3$-alkylene group; and Q is —OR$^1$; —SR$^2$; —S(O)R$^2$; —S(O)$_2$R$^2$; —NR$^3$R$^4$; —NH—(CH$^2$)$_2$—NR$^3$R$^4$ or halogen;

R$^1$ is hydrogen; alkyl; allyl; dimethylphosphonylmethyl; 2,3-epoxy-1-propyl; (R)-2,3-dihydroxy-1-propyl; (S)-2,3-dihydroxy-1-propyl; 1,3-dihydroxy-2-propyl; 3-hydroxy-2-hydroxymethyl-1-propyl; 2-methoxyethoxymethyl; 2,2-dimethyl-1,3-dioxolan-4-ylmethyl or a group A$^1$-Q$^1$; and Q$^1$ represents —O-alkyl; —CN; —C(O)$_2$H; —C(O)$_2$-alkyl; —C(O)—NR$^3$R$^4$; —S-alkyl; —S(O)-alkyl; —S(O)$_2$-alkyl and in case that A$^1$ represents an 1,2-ethylen- or 1,3-propylen group, Q$^1$ is —OH or —NR$^3$R$^4$;

R$^3$, R$^4$ independently represent hydrogen or alkyl; or

R$^3$ and R$^4$ together with the nitrogen atom to which they are attached form a 5 to 7 membered, saturated or unsaturated ring, which is unsubstituted or substituted by a methyl group and wherein one additional nitrogen- or oxygen atom is present, and the remaining atoms being carbon atoms;

R$^2$ is alkyl; dimethylphosphonylmethyl; 2,3-epoxy-1-propyl; 2,3-dihydroxy-1-propyl; 2,2-dimethyl-1,3-dioxolan-4-ylmethyl or A$^1$-Q$^1$;

Y is aryl or heteroaryl, which are both unsubstituted or substituted one, two or three times by halogen; —CH$_2$OR$^5$; —R$^5$; —OR$^5$; —NR$^6$R$^7$; —SR$^5$; —S(O)R$^5$;

—S(O)$_2$R$^5$; —S(O)NHR$^5$; —S(O)$_2$NHR$^5$; —S(O)NR$^6$R$^7$; —S(O)$_2$NR$^6$R$^7$; —C(O)NHR$^5$; —C(O)NR$^6$R$^7$; or CN;

R$^5$ is hydrogen; or
  alkyl, which is unsubstituted or substituted with OH; —O-alkyl or —NR$^6$R$^7$;
  with the proviso that two heteroatoms are not connected to the same carbon atom;

R$^6$, R$^7$ independently represent hydrogen or alkyl; or

R$^6$ and R$^7$ together with the nitrogen atom to which they are attached form a 5 to 7 membered, saturated or unsaturated ring, which is unsubstituted or substituted by a methyl group and wherein one additional nitrogen- or oxygen atom is present, and the remaining atoms being carbon atoms;

Z is halogen; —OH; —O-allyl; alkyl; methoxymethoxy; (2-methoxyethoxy)methyloxy; methylthio; ethoxymethoxy; methylendioxy; ethynyl; trimethylsilyl-ethynyl; or
  —O-alkyl, wherein the alkyl group is unsubstituted or substituted with pyridinyl; or
benzyloxy which is unsubstituted or substituted by halogen; methoxy; ethoxy; methylenedioxy; —CN; —NO$_2$; or —C(O)$_2$H; and n is 1 or 2; and
pharmaceutically acceptable salts thereof.

The compounds of the present invention are inhibitors of protein tyrosin kinases, especially of c-met and src family kinases, and may therefore be used as active agents in the prevention and therapy of diseases mediated by said kinases; for example transplant rejection, inflammatory bowel syndrome, rheumatoid arthritis, psoriasis, restenosis, allergic asthma, Alzheimers disease, Parkinson, stroke, osteoporosis, cancer, and benign hyperplasias.

Objects of the present invention are the compounds of formula (I) and pharmaceutically acceptable salts and their enantiomeric forms, the preparation of the above-mentioned compounds, medicaments containing them and their manufacture as well as the use of the above-mentioned compounds in the control or prevention of illnesses, especially of illnesses and diseases mentioned above or in the manufacture of corresponding medicaments.

As used herein, the term "alkyl" means a straight-chain or branched-chain hydrocarbon saturated containing from 1 to 6, preferably from 1 to 4, more preferably from 1 to 3 carbon atoms, such as methyl, ethyl, n-propyl, isopropyl, n-butyl, 2-butyl, tert-butyl, n-pentyl, n-hexyl as well as their isomers.

A "C$_1$–C$_3$-alkylen group" as used herein represents a bivalent saturated linear or branched hydrocarbon having 1, 2 or 3 carbon atoms. Preferably said C$_1$–C$_3$-alkylen group is linear.

Examples are a methylene-, ethylene-, propylene- or isopropylene group.

The term "aryl" as used herein denotes a 6 to 10 membered mono- or bicyclic, aromatic hydrocarbon ring. Examples are phenyl, naphtyl or indenyl. Preferably said "aryl" group is phenyl.

The term "heteroaryl" as used herein denotes a 5 to 10 membered mono- or bicyclic, aromatic hydrocarbon ring, wherein one, two or three, preferably one or two carbon atoms may be replaced by nitrogen, oxygen or sulfur. Examples are furyl, thienyl, pyrrolyl, isoxazolyl, imidazolyl, pyridyl, pyrimidinyl, benzofuranyl, indolyl. Preferably said "heteroaryl" is pyridyl.

"Halogen" means fluorine, chlorine, bromine, or iodine.

An embodiment of the present invention are compounds of formula (I), wherein

K, L are both chlorine;
X is hydrogen; alkyl or —O-alkyl, which alkyl groups are substituted by —OH;
Y, Z and n are as defined above; and
physiologically acceptable salts thereof.

Another embodiment of the present invention are compounds of formula (J), wherein K, L are both chlorine;
X is hydrogen; alkyl or —O-alkyl, which alkyl groups are substituted by —OH;
Z is halogen or ethynyl;
Y is phenyl, which is unsubstituted or once substituted by halogen; —CH$_2$OR$^5$; —R$^5$; —OR$^5$; —NR$^6$R$^7$; —SR$^5$; —S(O)R$^5$; —S(O)$_2$R$^5$; —S(O)NHR$^5$; —S(O)$_2$NHR$^5$; —S(O)NR$^6$R$^7$; —S(O)$_2$NR$^6$R$^7$; —C(O)NHR$^5$; —C(O)NR$^6$R$^7$; or CN;

R$^5$ is hydrogen; or
  alkyl, which is unsubstituted or substituted with OH; —O-alkyl or —NR$^6$R$^7$;
  with the proviso that two heteroatoms are not connected to the same carbon atom;

R$^6$, R$^7$ independently represent hydrogen or alkyl;
n is 1; and
pharmaceutically acceptable salts thereof.

Such compounds are for example:

2-(2,6-dichlorophenyl)-4-(3-bromophenyl)-5-(2-[4-(2-diethylamino-ethoxy)phenylamino]pyrimidin-4-yl)-N—H-imidazole, 2-(2,6-dichlorophenyl)-4-(3-chlorophenyl)-5-(2-[4-(2-diethylamino-ethoxy)phenylamino]pyrimidin-4-yl)-N—H-imidazole, 2-(2,6-dichlorophenyl)-4-(3-chlorophenyl)-5-(2-[4-(2-hydroxyethoxy)phenyl-amino]pyrimidin-4-yl)-N—H-imidazole, 2-(2,6-dichlorophenyl)-4-(3-chlorophenyl)-5-(2-[4-dimethylaminophenyl-amino]pyrimidin-4-yl)-N—H-imidazole, 2-(2,6-dichlorophenyl)-4-(3-chlorophenyl)-5-(2-[4-(N-(2-hydroxyethyl)-sulfamoyl)phenylamino]-pyrimidin-4-yl)-N—H-imidazole, 2-(2,6-dichloro-4-hydroxymethylphenyl)-4-(3-chlorophenyl)-5-(2-[4-(2-diethylaminoethoxy)-phenylamino]pyrimidin-4-yl)-N—H-imidazole, 2-(2,6-dichloro-4-hydroxymethylphenyl)-4-(3-chlorophenyl)-5-(2-[4-(2-hydroxyethoxy)-phenylamino]pyrimidin-4-yl)-N—H-imidazole, 2-(2,6-dichloro-4-[2-hydroxyethoxy]phenyl)-4-(3-chlorophenyl)-5-(2-[4-(2-diethylaminoethoxy)-phenylamino]pyrimidin-4-yl)-N—H-imidazole, 2-(2,6-dichloro-4-[2-hydroxyethoxy]phenyl)-4-(3-chlorophenyl)-5-(2-[4-methylsufinyl-phenylamino]pyrimidin-4-yl)-N—H-imidazole, 2-(2,6-dichloro-4-[2-hydroxyethoxy]phenyl)-4-(3-chlorophenyl)-5-(2-[4-(N-(2-hydroxyethyl)-sulfamoyl)phenylamino]pyrimidin-4-yl)-N—H-imidazole, 2-(2,6-dichlorophenyl)-4-(4-chlorophenyl)-5-(2-[4-(2-diethylaminoethoxy)-phenylamino]pyrimidin-4-yl)-N—H-imidazole, 2-(2,6-dichlorophenyl)-4-(4-chlorophenyl)-5-(2-[4-hydroxyphenyl-amino]pyrimidin-4-yl)-N—H-imidazole, 2-(2,6-dichlorophenyl)-4-(4-chlorophenyl)-5-(2-[4-methoxyphenyl-amino]pyrimidin-4-yl)-N—H-imidazole, 2-(2,6-dichlorophenyl)-4-(4-chlorophenyl)-5-(2-[4-ethoxyphenyl-amino]pyrimidin-4-yl)-N—H-imidazole, 2-(2,6-dichlorophenyl)-4-(3-ethynylphenyl)-5-(2-[4-(2-diethylamino-ethoxy)phenylamino]pyrimidin-4-yl)-N—H-imidazole, 2-(2,6-dichlorophenyl)-4-(3-ethynylphenyl)-5-(2-[4-(2-hydroxyethoxy)-phenylamino]pyrimidin-4-yl)-N—H-imidazole, or 2-(2,6-dichloro-4-[2-hydroxyethoxy]phenyl)-4-(3-ethynylphenyl)-5-(2-[4-(2-diethylaminoethoxy)-phenylamino]pyrimidin-4-yl)-N—H-imidazole.

Another embodiment of the present invention are compounds of formula (I), wherein K, L are both chlorine;
X is hydrogen;
Z is halogen;
Y is phenyl, which is substituted by —NR⁶R⁷, wherein
R⁶ and R⁷ together with the nitrogen atom to which they are attached form a 5 to 7 membered, saturated or unsaturated ring, which is unsubstituted or substituted by a methyl group and wherein one additional nitrogen- or oxygen atom is present, and the remaining atoms being C-atoms;
n is 1; and
pharmaceutically acceptable salts thereof.

Such compounds are for example:

2-(2,6-dichlorophenyl)-4-(4-chlorophenyl)-5-(2-[4-morpholinophenyl-amino]pyrimidin-4-yl)-N—H-imidazole, or 2-(2,6-dichlorophenyl)-4-(3-chlorophenyl)-5-(2-[4-morpholinophenyl-amino]pyrimidin-4-yl)-N—H-imidazole.

Another embodiment of the present invention are compounds of formula (I), wherein K, L are both chlorine;
X is hydrogen;
Z is halogen;
Y is heteroaryl, which is unsubstituted or substituted one, two or three times by halogen; —CH₂OR⁵; —R⁵; —OR⁵; —NR⁶R⁷; —SR⁵; —S(O)R⁵; —S(O)₂R⁵; —S(O)NHR⁵; —S(O)NR⁶R⁷; —S(O)₂NR⁶R⁷; —C(O)NHR⁵; —C(O)NR⁶R⁷; or CN;
R⁵ is hydrogen; or
alkyl, which is unsubstituted or substituted with OH; —O-alkyl or —NR⁶R⁷;
with the proviso that two heteroatoms are not connected to the same carbon atom;
R⁶, R⁷ independently represent hydrogen or alkyl; or
R⁶ and R⁷ together with the nitrogen atom to which they are attached form a 5 to 7-membered, saturated or unsaturated ring, which is unsubstituted or substituted by a methyl group and wherein one additional nitrogen- or oxygen atom is present, and the remaining atoms being C-atoms;
n is 1; and
pharmaceutically acceptable salts thereof Another embodiment of the present invention are compounds of formula (I), wherein K, L are both chlorine;
X is hydrogen;
Z is halogen;
Y is pyridinyl, which is unsubstituted or substituted by alkyl;
n is 1; and
pharmaceutically acceptable salts thereof.

Such a compound is for example:

2-(2,6-dichlorophenyl)-4-(4-chlorophenyl)-5-(2-[4-pyridinylamino]pyrimidin-4-yl)-N—H-imidazole.

Still another embodiment of the present invention is a process for the production of the compounds according to claim 1, wherein compounds of the general formula (VI)

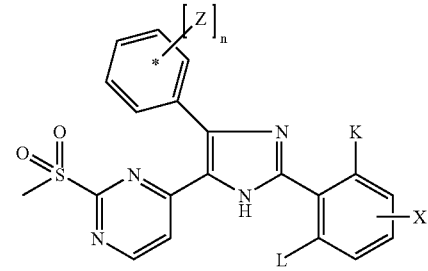

(VI)

are reacted with a compound of the formula Y—NH₂ to give the compounds of formula (I); the substituents K, L, X, Y, Z as well as n having the significances given above; and wherein the compounds of formula (VI) are obtained by oxidation of the sulfide group of the thioethers, described by the general formula (V)

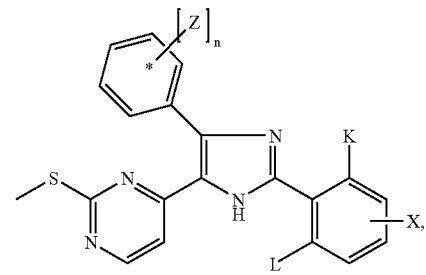

(V)

whereby the compounds of formula (V) are obtained by N-deoxygenation of compounds of the general formula (IV)

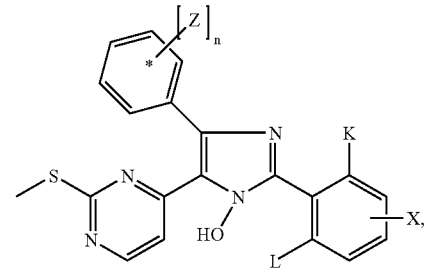

(IV)

and said compounds of the general formula (IV) being obtained by reacting a compound of the general formula (II)

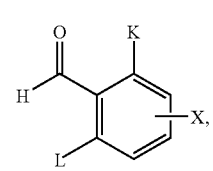

(II)

with a compound of the general formula (III)

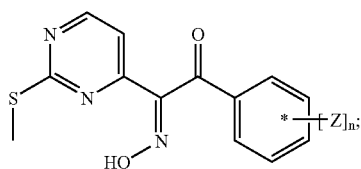

(III)

isolating said compounds of formula (I) from the reaction mixture, and c) if desired turning them into a pharmaceutically acceptable salt by addition of suitable acids or bases.

Compounds of the general formula (I) can be prepared by reacting a compound of the general formula (VI) with an amine Y—NH$_2$, wherein K, L, X, Y, Z and n have the significance as defined herein before, at a temperature in the range of 100 to 250° C. and subsequent isolation of said compound. Preferably stoichiometric amounts or an excess of said amines are used. The reaction can be performed without solvent or in a solvent like N-methyl pyrrolidone, dioxane, dimethoxyethane or toluene and by conventional heating or heating in a microwave reactor.

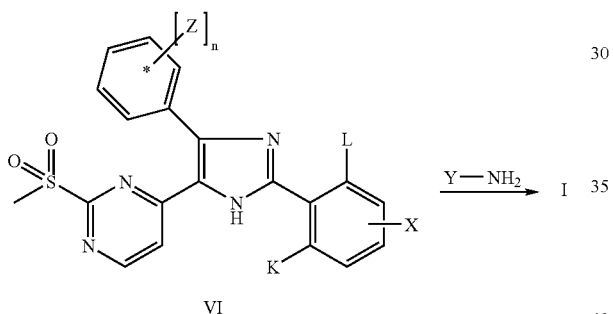

VI

Compounds of the general formula (VI) can be obtained by oxidation of the sulfide group of the thioethers, described by the general formula (V). For the synthesis of the sulfones of the general formula (VI) oxone™ is preferably used but 3-chloroperbenzoic acid works as well.

The thioethers of the general formula (V)

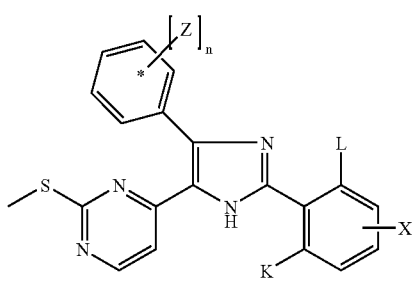

V can be obtained by N-deoxygenation of compounds of the general formula (IV). This reaction is preferably carried out using ethyl bromoacetate in the presence of triethylamine (Somei, M., and Tsuchiya, M., Chem. Pharm. Bull. 29 (1981) 3145–3157). Alternatively, this reduction can be achieved by the use of triethylphosphite in dimethylformamide.

A compound of the general formula (IV) can be obtained by reacting a compound of the general formula (III) with a compound of the general formula (II), wherein the substituents K, L, X and Z as well as n have the significances as defined hereinbefore. This reaction is a condensation and is preferably carried out in the presence of ammonia, using methods which are known for other aldehydes.

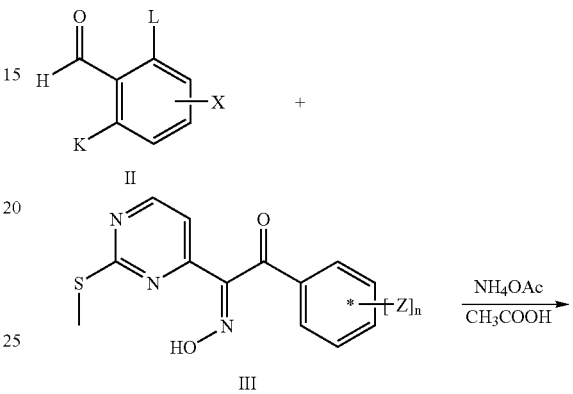

II

III

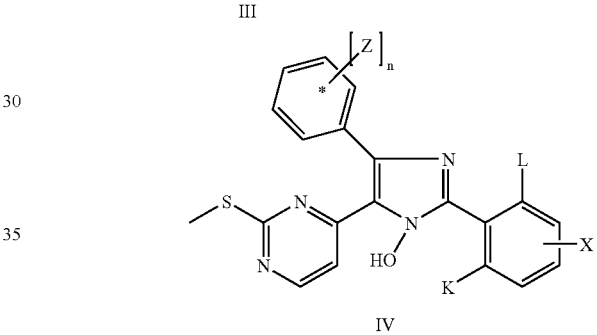

IV

A further embodiment of the invention is the use of a compound of the general formula (II), wherein the substituents K, L and X have the significances as defined hereinbefore, for the manufacture of a compound of the general formula (I) as described in the above-mentioned process.

Formula (I) represents 2-phenyl-4-phenyl-5-(4-pyrimidinyl)-1H-imidazoles which are the tautomers of 2-phenyl-5-phenyl-4-(4-pyrimidinyl)-1H-imidazoles. Both tautomers represent the same structure, their nomenclature may be used interchangeably and both tautomers are part of the invention.

The compounds of the general formula (I) can contain one or several chiral centers and can then be present in a racemic or in an optically active form. The racemates can be separated according to known methods into the enantiomers. For instance, diastereomeric salts which can be separated by crystallization are formed from the racemic mixtures by reaction with an optically active acid such as e.g. D- or L-tartaric acid, mandelic acid, malic acid, lactic acid or camphorsulfonic acid. Alternatively separation of the enantiomers can also be achieved by using chromatography on chiral HPLC-phases which are commercially available.

The compounds according to the present invention may exist in the form of their pharmaceutically acceptable salts. The term "pharmaceutically acceptable salt" as used herein before refers to conventional acid-addition salts or base-addition salts that retain the biological effectiveness and properties of the compounds of formula (I) and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e., a drug) into a salt is a technique well known to pharmaceutical chemists to obtain improved physical and chemical stability, hygroscopicity, flowability and solubility of compounds (see, e.g., Ansel, H., et. al., Pharmaceutical Dosage Forms and Drug Delivery Systems, 6th ed., (1995), pp. 196 and 1456–1457).

The activity of the compounds according to this invention as inhibitors for the src-family tyrosine kinases and c-met kinase can be assessed by using the following assays.

SRC-Inhibitor-Assay Parameters:

| Reaction mixture: | |
|---|---|
| ATP | 5 µM |
| Peptide (Ro + Ja133-Ro): | 10 µM |
| Ja133-Ro | 196 nM |
| Ro | 9.8 µM |
| PT66 | 230 ng/ml |

Assay buffer: 4 mM MgCl2
2 mM TCEP
50 mM HEPES
0.1% Tween 20
pH 7.3
Enzyme: 2.5 U/ml
Inhibitor: max. 25 µM
min. 0.42 nM Material:
Eu-labelled phosphotyrosine antibody:—for Lck Cisbio Mab PT66-K,
for Src EG&G Wallac PT66 Eu-W1024 (all commercially available).
Peptides: Ro: $NH_2$-A-E-E-E-I-Y-G-E-F-E-A-K-K-K-K-$CONH_2$ (SEQ ID NO: 1), and Ja133-Ro: Ja133-G-Aminocaprylic acid-A-E-E-E-I-Y-G-E-F-E-A-K-K-K-K-$CONH_2$ (SEQ ID NO: 2) wherein Ja133 is LightCycler-Red 640-N-hydroxy succinimide ester; whereby both peptides were synthesized by an optimized solid phase peptide synthesis protocol (Merrifield, Fed. Proc. Fed. Amer. Soc. Exp. Biol. 21 (1962) 412) on a Zinsser SMP350 peptide synthesizer. Shortly, the peptide was assembled on 160 mg (22.8 µmol scale) of a Rink-Linker modified polystyrene solid phase by repeatedly conjugating an twenty fold excess of aminoacids each protected by temporary piperidine labile Fmoc- and permanent acid labile tert-Bu-, BOC- and Otert-Bu-groups depending on the side chain function. The substrate sequence AEEEIYGEFEAKKKK (SEQ ID NO: 1) was N-terminal additionally mounted with the spacer amino acids Aminocaprylic acid and Glycin. After cleavage of the N-terminal temporary protecting group the still attached and protected peptide was labeled with a 1.5 fold amount of LightCycler-Red 640-N-hydroxy succinimide ester (purchased by Roche Diagnostics GmbH) and triethylamine. After 3 hrs. the resin was washed with Dimethylformamide and Isopropanol until the eluates of the blue resin got colourless. The fully protected and labeled peptide was removed from the solid phase and released from the permanent protecting groups by treatment with a mixture of 80% trifluoracetic acid, 10% Ethanedithiol, 5% Thioanisol and 5% Water. The substrate was finally isolated by a preparative reverse phase HPLC purification. The purification yielded 12.2 mg RP-HPLC single peak pure blue material (lyophilisate). The identity was proven by MALDI mass spectroscopy [2720.0].

Enzymes: Upstate Lck ($p56^{lck}$, active), Upstate Src ($p60^{c-src}$, partially purified) were purchased from UBI.

Time-resolved Fluorescence Assay: Reader: Perkin Elmer, Wallac Viktor 1420-040 multilabel counter; Liquid handling system: Beckman Coulter, Biomek 2000.

ATP, Tween 20, HEPES were purchased from Roche Molecular Biochemicals, $MgCl_2$ and $MnCl_2$ were purchased from Merck Eurolab, TCEP was purchased from Pierce, 384 Well low volume fluorescence plates was purchased from Falcon.

Assay Description:
At first the enzyme is pre-incubated for 15 min. at 15° C. in aqueous solution with corresponding amounts of inhibitors according to this invention. Then the phosphorylation reaction is started by adding a reaction mixture, containing ATP, Peptide and PT66, and subsequent shaking. The proceeding of this reaction is immediately monitored using time resolved fluorescence spectroscopy in a suitable well plate reader.

The $IC_{50}$-values can be obtained from the reaction rates by using a non-linear curve fit (Excelfit).

Results:

| Example | $IC_{50}$ src [µM] |
|---|---|
| H3.1.1 | 0.0244 |
| H2.2.1 | 0.0005 |
| H1.1 | 0.0067 |
| H2.1.4 | 0.0233 |
| H2.1.3 | 0.031 |
| H4.1.2 | 0.0333 |
| H2.3.2 | 0.3306 |
| H2.3.3 | 0.0067 |
| H2.3.1 | 0.0016 |

C-met-Inhibitor-Assay:

Assay Principle
C-met is a typical tyrosine kinase which is involved in metastasis, proliferation/apoptosis and angiogenesis of tumors. The assay is an ELISA type assay measuring the phosphorylation of c-met using a phospho-tyrosine specific antibody.

Cell lysate of human colon adenocarcinoma HT29 known for its high content of c-met is bound to the wells of a microtiterplate (MTP) via an anti-hHGF receptor antibody (anti-hHGFR). ATP-phosphorylation of c-met is detected in presence or absence of the test compounds by using a phospho-tyrosine mouse IgG and a POD labeled goat anti-mouse IgG detection system. Using the classical POD substrate TMB, an absorption at 450 nm/620 nm is used to calculate enzymatic activity.

Materials:
  Plates: 96-well polystyrene plates (NUNC) streptavidin-coated microtiter plates Cell line/Lysate: HT29 (ATCC HTB-38), human colon adenocarcinoma (confluence: 2.5× $10^5$ cells/cm$^2$) are washed with PBS and incubated with Lysis buffer for 10 min on ice. Supernatent is collected and diluted with TBS. Lysate is shockfrozen in liquid nitrogen and stored at −80° C.)
  Reagents (all working solutions are kept at 4° C., unless stated otherwise):
anti-hHGFR detection stock solution: 50 μg/ml (R&D Systems, Cat.No. BAF 358) antibody final conc.: 1 μg/ml
p-Tyr (PY99) mouse stock solution: 200 μg/ml (Santa Cruz Biotechnology, monoclonal IgG2b Cat.No. SC-7020) final conc.: 0.2 μg/ml
goat-anti-mouse IgG: 2 ml (BIO RAD, Cat.No. 170-6516) (H+L)-HRP Conjugate; final conc.: 1:2000
Blocking Reagent: Roche Diagnostics GmbH, Cat.No.1112589 for ELISA diluted 1:10 in TBS
ATP: Adenosine-5'-triphosphate, stock solution 10 mM, stock solution 10 mM (Roche
Diagnostics GmbH, Cat.No. 127531) final conc.: 40 μM
TBS: Tris-buffered saline, 50 mM TRIS pH 7.5 (Roche Diagnostics GmbH, Cat.No. 708976), 150 mM NaCl (SIGMA, Cat.No. S-3014)
Wash buffer TBS-T: Tris-buffered saline, 50 mM TRIS pH 7.5 150 mM NaCl, containing 0.5% Tween20
Kinase buffer: Tris-buffered saline, 50 mM TRIS pH 7.5, 100 mM NaCl, 60 mM $MgCl_2$ (SIGMA Chemical Company, Cat.No. M-1028)
Lysis buffer: 50 mM TRIS pH 7.5 containing 1% Nonidet P40 (Roche Diagnostics GmbH, Cat.No.1754599) 0.5% Deoxycholic acid (SIGMA Chemical Company, Cat.No. D-6750)
final conc.: 1 mM 1 mM PMSF stock solution 70 mM (Roche Diagnostics GmbH,
Cat.No.837091 40 μl/ml Complete (Roche Diagnostics GmbH, Cat.No. 1836145) Final conc.: 40 μl/ml
TMB: Tetramethylbenzidine (Intergen Company, Cat.No. 91000)
Samples: 10 mM in DMSO (stored at −20° C.), thawed at room temperature
Procedure:
  Add 50 μl of anti-hHGFR detection antibody in blocking reagent to assay plate (final conc. 1 μg/ml), incubate assay plate for 60 min at room temperature on an MTP shaker.
  Remove anti-hHGFR detection antibody solution from assay plate.
  Add 250 μl blocking reagent per well to assay plate, incubate assay plate for 20 h, at 4° C.
  Remove blocking reagent from assay plate.
  Add 50 μl of HT29 lysate, incubate assay plate for 180 min, at 4° C. on an MTP shaker.
  Wash assay plate with 2×200 μl TBS buffer per well.
  Add 40 μl of 0.2% DMSO in kinase buffer to assay plate.
  Add 40 μl sample solution (dissolved in kinase buffer—final conc. 22.5 μM).
  Dissolve samples (1:3 ratio) in MTP.
  Add 10 μl ATP dissolved in kinase buffer (200 μM) to samples (final conc. 40 μM ATP). Positive control: add 40 μl kinase buffer plus 10 μl 200 μM ATP. Negative control: add 40 μl kinase buffer plus 10 μl kinase buffer without ATP. Incubate assay plate for 60 min at room temperature on an MTP shaker.
  Wash assay plate with 2×200 μl TBS buffer and 2×200 μl blocking reagent per well.
  Add 50 μl of P-Tyr (PY99) mouse monoclonal $IgG_{2b}$ in blocking reagent (final conc. 200 ng/ml) to assay plate, incubate assay plate over night at 4° C. on an MTP shaker.
  Wash assay plate with 2×200 μl TBS buffer and 2×200 μl blocking reagent per well.
  Add 50 μl of goat anti-mouse IgG (H+L)-HRP conjugate in blocking reagent (1:2000 ratio), incubate assay plate for 60 min at room temperature on an MTP shaker.
  Wash assay plate with 6×200 μl TBS-T buffer per well.
  Add 50 μl TMB solution, incubate for 30 min at room temperature on an MTP shaker, add 25 μl 1 M $H_2SO_4$.
  Measure optical density (E) at 450 nm/620 nm.
  Calculate % inhibition as:

$$1-[(E_{sample}-E_{negative}\ control)/(E_{positive\ control}-E_{negative\ Control})\times 100]$$

Results:

| Example | IC$_{50}$ C-met [μM] |
|---|---|
| H3.1.1 | 0.609 |
| H2.2.1 | 0.004 |
| H1.1 | 0.005 |
| H2.1.4 | 0.084 |
| H2.1.3 | 0.167 |
| H4.1.2 | 0.09 |

Consequently the compounds of formula (I) and the pharmaceutically acceptable salts of the compounds of formula (I) can be used as medicaments, e.g. in the form of pharmaceutical preparations. The pharmaceutical preparations can be administered orally, e.g., in the form of tablets, coated tablets, dragees, hard and soft gelatine capsules, solutions, emulsions or suspensions. The administration can, however, also be effected rectally, e.g. in the form of suppositories or parenterally, e.g. in the form of injection solutions.

The compounds of formula (I) can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

A preferred pharmaceutical preparation was obtained by using the following procedure:
Weigh 4.0 g glass beads in custom made tube GL 25, 4 cm (the beads fill half of the tube).
Add 50 mg compound, disperse with spatulum and vortex.
Add 2 ml gelatin solution (weight beads:gelatin solution=2:1) and vortex.

Cap and wrap in aluminium foil for light protection.
Prepare a counter balance for the mill.
Mill for 4 hours, 20/s in a Retsch mill (for some substances up to 24 hours at 30/s).
Extract suspension from beads with two layers of filter (100 µm) on a filter holder, coupled to a recipient vial by centrifugation at 400 g for 2 min.
Move extract to measuring cylinder.
Repeat washing with small volumes(here 1 ml steps) until final volume is reached or extract is clear.
Fill up to final volume with gelatin and homogenise.

The above described preparation yields micro-suspensions of the compounds of formula (I) with particle sizes between 1 and 10 µm and are suitable for oral applications.

A further preferred pharmaceutical preparation of the compounds according to the present invention is a tablet formulation by wet granulation, as follows:

Materials

| Item | Ingredients | mg/tablet | | | |
|---|---|---|---|---|---|
| 1. | Compound of formula (I) | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Still another preferred pharmaceutical preparation is the manufacture of capsules, containing the compounds according to the present invention by the following procedure:

Materials

| Item | Ingredients | mg/capsule | | | |
|---|---|---|---|---|---|
| 1. | Compound of formula (I) | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The dosage of a compound according to this invention which is administered to a patient may vary within wide limits and will also have to be adjusted to the individual requirements in each particular case. The daily dosage may be administered as single dose or in divided doses and, in addition, the upper limit can also be exceeded when this is found to be indicated.

Therefore an object of the present invention is a pharmaceutical composition, containing one or more compounds of formula (I) together with pharmaceutically acceptable excipients.

Another object of the present invention is a pharmaceutical composition as described above for the inhibition of tumor growth.

Still another object of the present invention is the use of a compound of formula (I) for the treatment of cancer.

Still another object of the present invention is the use of a compound of formula (I) for the manufacture of medicaments for the treatment of diseases mediated by c-met- or src tyrosine kinases.

Still another object of the present invention is the use of a compound of formula (I) for the manufacture of medicaments for the inhibition of tumor growth.

The following examples and preparations illustrate the invention but are not intended to limit its scope.

EXAMPLES

A Synthesis of Substituted 2,6-dichlorobenzaldehydes

Example A1

2,6-dichloro-4-hydroxybenzaldehyde (A1)

Preparation of 3,5-dichlorotriisopropylsilyloxybenzene (A1.1)

To a solution of 200 g 3,5-dichlorophenol and 330 ml 2,6-lutidine in 3.0 l dry $CH_2Cl_2$ 400 g triisopropylsilyl triflate was added at 0° C. within 1 h and the mixture was stirred for additional 3 hours at this temperature. After hydrolysis with 1.0 l water the organic layer was washed with saturated NaCl, dried over $MgSO_4$ and evaporated to dryness (70° C./80 mbar). The residue was taken up in petrol ether and filtrated through SiGel to yield 360 g (92%) A1.1 as colorless oil.

$^1$H-NMR (250 MHz, $CDCl_3$) δ=1.03–1.15 (m, 18 H, $CH_3$); 1.16–1.35 (m, 3 H CH); 6.73–6.80 (m, 2 H, $CH_{arom.}$); 6.92–6.98 (m, 1 H, $CH_{arom.}$) $^{13}$C-NMR (62.9 MHz, $CDCl_3$) δ=12.7 (CH); 18.0 (CH3); 119.0, 121.6 ($CH_{arom.}$); 135.2, 157.4 ($C_{arom.}$)

Preparation of 2,6-dichloro-4-hydroxybenzaldehyde (A1) and 2,6-dichloro-4-triisopropylsilyloxy-benzaldehyde (A1.2)

To a solution of 360 g A1.1 in 2.6 l dry tetrahydrofurane 440 ml n-BuLi (2.7 M in hexane) was added under nitrogen keeping the temperature below −65° C. After stirring for 2 h at −70° C. 120 ml dry dimethylformamide was added keeping the temperature below −65° C. The mixture was allowed to warm up to room temperature overnight. After addition of 700 ml 4 M HCl the mixture was stirred vigorously for 1 h at room temperature. Then the phases were separated (addition of solid NaCl may be necessary) and the organic layer was dried over sodium sulphate and was reduced in vacuo. Recrystallization of the precipitate from toluene/tetrahydrofurane yielded 154 g (70%) A1, m.p. 229–230° C.

$^1$H-NMR (250 MHz, $DMSO-D_6$) δ=6.94 (s, 2 H, $CH_{arom.}$); 10.25 (s, 1 H, CH=O), 11.46 (s (br), 1 H, OH) $^{13}$C-NMR (62.9 MHz, $DMSO-D_6$) δ=117.0 ($CH_{arom.}$); 120.7, 137.8, 162.1 ($C_{arom.}$); 187.2 (CH=O)

Example A2

2,6-dichloro-4-hydroxymethylbenzaldehyde (A2)

Preparation of 3,5-dichloro(triisopropylsilyloxymethyl)benzene (A2.1)

An analogous reaction to that described in example A1.1, but starting with 3,5-dichlorobenzylic alcohol gave the title compound as a colorless oil in similar yield.

$^1$H-NMR (250 MHz, CDCl$_3$) δ=0.96–1.25 (m, 21 H, i-Pr); 4.78 (s, 2 H, OCH$_2$); 7.23 (s, 2 H, CH$_{arom.}$) $^{13}$C-NMR (62.9 MHz, CDCl$_3$) δ=12.1 (CH); 18.1 (CH$_3$); 64.0 (OCH$_2$); 124.2, 127.0 (C$_{arom.}$H); 134.9, 145.3 (C$_{arom.}$)

Preparation of 2,6-dichloro-4-(triisopropylsilyloxymethyl)benzaldehyde (A2.2)

To a solution of 70 g A2.1 in 220 ml dry tetrahydrofurane 131 ml n-BuLi (1.6 M in hexane) was added under nitrogen keeping the temperature below –70° C. After stirring for 45 minutes at –75° C. 28 ml dry dimethylformamide was added keeping the temperature below –65° C. The mixture was stirred additional 30 minutes at –75° C. and then was allowed to warm up 0° C. within 3 h. After 2 h at 0° C. 150 ml ice water and 150 ml ether were added. The phases were separated and the aqueous layer extracted with 100 ml ether. The combined organic layers were washed with aqueous NaCl dried over sodium sulphate and evaporated to dryness. Yield: 73 g (95%) A3.2 as a light brown oil, that solidifies an ice standing.

$^1$H-NMR (250 MHz, CDCl$_3$) δ=1.03–1.28 (m, 21 H, i-Pr); 4.82 (s, 2 H, OCH$_2$); 7.37 (s, 2 H, CH$_{arom.}$); 10.48 (s, 1 H, CH=O) $^{13}$C-NMR (62.9 MHz, CDCl$_3$) δ=12.0 (CH); 18.1 (CH$_3$); 63.6 (OCH$_2$); 126.8 (C$_{arom.}$H); 128.6, 137.2, 149.0 (C$_{arom.}$); 188.8 (CH=O)

Preparation of 2,6-dichloro-4-hydroxymethylbenzaldehyde (A2)

To a solution of 65 g (0.18 mol) A2.2 in 1100 ml ethanol at 50° C. 180 ml 0.25 N HCl was added and the mixture was stirred for 6 h at 85° C. The ethanol was removed in vacuo whereupon the product precipitates. 700 ml ethyl acetate/petrol ether (2:1) was added and the organic layer was washed with water and aqueous NaCl and dried over sodium sulphate. The solution was reduced to about 100 g and 200 ml warm petrol ether were added and shortly warmed up to 50° C. After standing at room temperature overnight the precipitated A2 was filtered off and washed with petrol ether/ethyl acetate (15:1). Yield: 24.3 g (66%). Purification of the mother liquor by column chromatography yielded another 4 g A2, m.p. 109–110° C.

$^1$H-NMR (250 MHz, CDCl$_3$) δ=1.99 (t, 4.4 Hz, 1 H, OH); 4.74 (d, 4.4 Hz, 2 H, OCH$_2$); 7.40 (s, 2 H, CH$_{arom.}$); 10.48 (s, 1 H, CH=O) $^{13}$C-NMR (62.9 MHz, CDCl$_3$) δ=63.4 (OCH$_2$); 127.5 (C$_{arom.}$H); 129.2, 137.4, 147.9 (C$_{arom.}$); 188.7 (CH=O)

Example A4

Preparation of methyl (3,5-dichloro-4-formylphenoxy)acetate (A4)

A mixture of 382 mg (2.0 mmol) A1, 337 mg (2.2 mmol) methyl bromoacetate and 387 mg (2.8 mmol) potassium carbonate in 6 ml dry acetone were stirred for 2 h at 60° C. After filtration and removal of the solvent the residue was purified by column chromatography on SiGel (hexane/ethyl acetate 4:1). Yield: 508 mg (97%) A4, colorless solid.

$^1$H-NMR (250 MHz, DMSO-D$_6$) δ=3.72 (s, 3 H, CH$_3$); 5.04 (s, 2 H, CH$_2$); 7.28 (s, 2 H, CH$_{arom.}$); 10.29 (s, 1 H, CH=O). $^{13}$C-NMR (62.9 MHz, DMSO-D$_6$) δ=52.1 (CH$_3$), 65.2 (CH$_2$); 116.5 (CH$_{arom.}$); 123.1, 137.5, 161.1 (C$_{arom.}$); 168.3 (C=O); 187.8 (CH=O).

B Synthesis of the "Weinreb"-Type Amides

Example B1

3-bromo-N-methoxy-N-methylbenzamide (B 1)

To an ice cooled solution of 48.9 g (0.491 mol) N,O-dimethylhydroxylamine hydrochloride and 140.0 ml (1.00 mol) triethylamine in 650 ml dry dichloromethane 100.0 g (0.447 mol) 3-bromobenzoyl chloride was added over a period of 30 minutes. After additional strirring for 30 minutes 370 ml water was added and the organic layer dried over sodium sulphate. Fractionated distillation in vacuo yielded 101.4 g (93%) B1, b.p. 114–129° C./0.07 mbar, as a colorless oil.

MS: 246 (API+) $^1$H-NMR (250 MHz, CDCl$_3$): δ=3.35 (s, 3H, NCH$_3$), 3.56 (s, 3H, OCH$_3$), 7.27 (t, 1H, 5-H), 7.58 (m, 1H, 4-H), 7.60 (m, 1H, 6-H), 7.82 (t, 1H, 2-H).

Example B2

3-chloro-N-methoxy-N-methylbenzamide (B2)

An analogous reaction to that described in example B1, but starting with 3-chlorobenzoyl chloride yielded B2.

MS: 200 (API+)

Example B3

4-chloro-N-methoxy-N-methylbenzamide (B3)

An analogous reaction to that described in example B2, but starting with 4-chlorobenzoyl chloride yielded B3.

MS: 200 (API+)

Example B4

3-iodo-N-methoxy-N-methylbenzamide (B4)

An analogous reaction to that described in example B1, but starting with 3-iodobenzoyl chloride yielded B4.

MS: 292 (API+)

C Synthesis of the "ethanones"

Example C1

1-(3-bromophenyl)-2-(2-methylthiopyrimidin-4-yl)-ethanone (C1)

19.8 ml (140 mmol) diisopropylamine were dissolved in 250 ml dry tetrahydrofurane and cooled to –75° C. and 87.6 ml of a solution of n-butyllithium (1.6 M in hexane, 140 mmol) was added over a period of 20 minutes. After stirring for 15 minutes at –75° C. a solution of 13.1 g (93 mmol) 2-methylthio-4-methylpyrimidine in 80 ml dry tetrahydrofurane was added within 30 minutes at –75° C. and the mixture was stirred for additional 15 minutes. Then a solution of 25.1 g (103 mmol) B1 was added within 30 minutes at –75° C. The mixture was allowed to warm up to room temperature and was poured on 600 ml ethyl acetate/water (1:1). The aqueous layer was extracted with 50 ml ethyl acetate and the combined organic layers were dried over sodium sulphate. Removal of the solvent in vacuo yielded 23.3 g (77%) C1, m.p. 98–101° C.

MS: M=325 (ESI+), M=323 (ESI−). $^1$H-NMR (250 MHz, CDCl$_3$): "enole" (75%) δ=2.62 (s, 3H, SCH$_3$), 5.97 (s, 1H, CH═C), 6.66 (s, 1H, 5-H-pyrimidine), 8.34 (d, 1H, 6-H-pyrimidine), 14.7 (s, 1H, OH). "keto" (25%) δ=2.52 (s, 3H, SCH$_3$), 4.35 (s, 2H, CH$_2$), 6.97 (d, 1H, 5-H-pyrimidin), 8.46 (d, 1H, 6-H-pyrimidin).

Example C2

1-(3-chlorophenyl)-2-(2-methylthiopyrimidin-4-yl)-ethanone (C2)

An analogous reaction to that described in example C1, but starting with B2 yielded C2.
MS: 279 (API+)

Example C3

1-(4-chlorophenyl)-2-(2-methylthiopyrimidin-4-yl)-ethanone (C3)

An analogous reaction to that described in example C1, but starting with B3 yielded C3.
MS: 279 (API+)

Example C4

1-(3-iodophenyl)-2-(2-methylthiopyrimidin-4-yl)-ethanone (C4)

An analogous reaction to that described in example C1, but starting with B4 yielded C4.
MS: 371 (API+)

Example C5

1-(3-trimethylsilylethynyl)-2-(2-methylthiopyrimidin-4-yl)-ethanone (C5)

To a solution of 16.3 g (44.0 mmol) C4 in 260 ml dry THF at 10° C. under nitrogen 1.5 g (2.2 mmol) bis-(triphenylphosphine)palladium-II-chloride, 900 mg (4.7 mmol) copper-I-iodide, 12 ml (85 mmol) trimethylsilylacetylene and 30 ml diisopropylamine were added and the mixture was stirred and successively allowed to warm up to room temperature. After stirring at room temperature overnight 260 ml water were added and the mixture was extracted twice with ether. The organic layer was separated, dried and evaporated to dryness. Column chromatography of the residue on SiGel (iso-hexane/ethyl acetate 3:1) yielded 12.5 g (83%) C5.
MS: 341 (API+)

D Synthesis of the "ketoximes"

Example D1

1-(3-bromophenyl)-2-(2-methylthiopyrimidin-4-yl)-2-hydroxyimino-ethanone (D1)

12.75 g (39.5 mmol) C1 were dissolved in a mixture of 173 ml glacial acid, 136 ml tetrahydrofurane and 17 ml water. After cooling to 5° C. a solution of 3.24 g (47.0 mmol) sodium nitrite in 25 ml water was added keeping the temperature between 5° C. and 10° C. The cooling was removed and the mixture stirred for 6 hours at room temperature. After removal of the solvent in vacuo 320 ml water and 320 ml ethyl acetate were added. The pH was adjusted to 8 with 3 N NaOH. The phases were separated and the aqueous layer was extracted with 50 ml ethyl acetate. The combined organic layers were dried over sodium sulphate and the solvent was removed in vacuo. The residue was treated with diethylether, filtered off and dried. Yield: 8.33 g (60%) D1, m.p. 156–158° C.

MS: M=352 (ESI+), M=340 (ESI−). $^1$H-NMR (250 MHz, D$_6$-DMSO): δ=2.20 (s, 3H, SCH$_3$), 7.54 (t, 1H, 5-H—BrPh), 7.66 (d, 1H, 5-H-pyrimidine), 7.81(m, 1H), 7.92 (m, 2H), 8.70 (d, 1H, 6-H-pyrimidine), 12.9 (s, 1H, OH).

Example D2

1-(3-chlorophenyl)-2-(2-methylthiopyrimidin-4-yl)-2-hydroxyimino-ethanone (D2)

An analogous reaction to that described in example D1, but starting with C2 yielded D2 in 88% yield.
MS: 308 (API+)

Example D3

1-(4-chlorophenyl)-2-(2-methylthiopyrimidin-4-yl)-2-hydroxyimino-ethanone (D3)

An analogous reaction to that described in example D1, but starting with C3 gave D3 in 76% yield.
MS: 308 (API+)

Example D4

1-(3-trimethylsilylethynyl)-2-(2-methylthiopyrimidin-4-yl)-2-hydroxyimino-ethanone (D4)

An analogous reaction to that described in example D1, but starting with C5 gave D4 in 54% yield, m.p. 140–145° C.

MS: 370 (API+), 368 (API−)

E Synthesis of the "N-hydroxy imidazoles"

Example E1.1

2-(2,6-dichlorophenyl)-4-(3-bromophenyl)-5-(2-methylthiopyrimidin-4-yl)-N-hydroxy-imidazole (E1.1)

27.9 g (79.3 mmol) D1, 14.6 g (83.2 mmol) 2,6-dichlorobenzaldehyde and 61.0 g (793 mmol) ammonium acetate were dissolved in 550 ml glacial acid and stirred at 100° C. for 150 minutes. The glacial acid was distilled off in vacuo and the residue was treated with ethyl acetate/water and justified at pH 8 with concentrated aqueous ammonia. The precipitate was filtered off, washed with ethyl acetate and dried to yield 24.8 g (62%) E1, m.p. 251–253° C. The aqueous layer was extracted with ethyl acetate and the combined organic layers dried over sodium sulphate. Removal of the solvent in vacuo and treatment with diethylether yielded another 8.9 g (22%) E1.1.

MS: M=509 (API+), 507 (API−)

Example E2.1

2-(2,6-dichlorophenyl)-4-(3-chlorophenyl)-5-(2-methylthiopyrimidin-4-yl)-N-hydroxy-imidazole (E2.1)

An analogous reaction to that described in example E1.1, but starting with D2 gave E2.1 in 85% yield.
MS: M=465 (API+), 463 (API−)

Example E2.2

2-(2,6-dichloro-4-hydroxymethylphenyl)-4-(3-chlorophenyl)-5-(2-methylthio-pyrimidin-4-yl)-N-hydroxy-imidazole (E2.2)

An analogous reaction to that described in example E1.1, but starting with D2 and A2 gave E2.2 in 67% yield.
MS: M=495 (API+), 493 (API−)

Example E2.3

2-(2,6-dichloro-4-[methoxycarbonylmethoxy]phenyl)-4-(3-chlorophenyl)-5-(2-methylthiopyrimidin-4-yl)-N-hydroxy-imidazole (E2.3)

An analogous reaction to that described in example E1.1, but starting with D2 and A4 gave E2.3 in 98% yield.
MS: M=553 (ESI+), 551 (ESI−)

Example E3.1

2-(2,6-dichlorophenyl)-4-(4-chlorophenyl)-5-(2-methylthiopyrimidin-4-yl)-N-hydroxy-imidazole (E3.1)

An analogous reaction to that described in example E1.1, but starting with D3 gave E3.1 in 96% yield.
MS: M=465 (API+), 463 (API−)

Example E4.1

2-(2,6-dichlorophenyl)-4-(3-trimethylsilylethynylphenyl)-5-(2-methylthio-pyrimidin-4-yl)-N-hydroxy-imidazole (E4.1)

An analogous reaction to that described in example E1.1, but starting with D4 gave E4.1 in 61% yield.
MS: M=525 (API+), 523 (API−)

Example E4.2

2-(2,6-dichloro-4-[methoxycarbonylmethoxy]phenyl)-4-(3-trimethylsilylethynyl-phenyl)-5-(2-methylthiopyrimidin-4-yl)-N-hydroxy-imidazole (E4.2)

An analogous reaction to that described in example E1.1, but starting with D4 and A4 gave E4.2 in 80% yield.
MS: M=541 (ESI+), 539 (ESI−)

F Synthesis of the "N—H imidazoles"

Example F1.1

2-(2,6-dichlorophenyl)-4-(3-bromophenyl)-5-(2-methylthiopyrimidin-4-yl)-N—H-imidazole (F1.1)

78.1 g (130 mmol) E1.1, 59.8 g (391 mmol) methyl bromoacetate and 181.6 ml (1.3 mol) triethylamine were dissolved in 3.35 l methanol and stirred at 60° C. overnight. After removal of the solvent in vacuo the residue was partitionated between ethyl acetate/water. The organic layer was dried over sodium sulphate evaporated to dryness an the residue was treated with diisopropyylether, filtered off and dried. Yield: 44.1 g (69%) F1, m.p. 183–186° C.

MS: M=493 (ESI+), M=491 (ESI−) $^1$H-NMR (250 MHz, $D_6$-DMSO): δ=2.18 (s, 3H, $SCH_3$), 7.43 (t, 1H, Ar—H), 7.5–7.8 (m, 5H, Ar—H), 7.87 (s, 1H, 2-H—BrPh), 8.56 (d, 1H, 6-H-pyrimidine), 13.4 (s, 1H, OH).

Example F2.1

2-(2,6-dichlorophenyl)-4-(3-chlorophenyl)-5-(2-methylthiopyrimidin-4-yl)-N—H-imidazole (F2.1)

An analogous reaction to that described in example F1.1, but starting with E2.1 gave F2.1 in 64% yield.
MS: M=449 (API+), 447 (API−)

Example F2.2

2-(2,6-dichloro-4-hydroxymethylphenyl)-4-(3-chlorophenyl)-5-(2-methylthiopyrimidin-4-yl)-N—H-imidazole (F2.2)

An analogous reaction to that described in example F1.1, but starting with E2.2 gave F2.2 in 98% yield.
MS: M=479 (API+), 477 (API−)

Example F2.3

2-(2,6-dichloro-4-[methoxycarbonylmethoxy]phenyl)-4-(3-chlorophenyl)-5-(2-methylthiopyrimidin-4-yl)-N—H-imidazole (F2.3)

An analogous reaction to that described in example F1.1, but starting with E2.3 gave F2.3 in quantitative yield.
MS: M=535 (ESI+)

Example F2.4

2-(2,6-dichloro-4-[2-hydroxyethoxy]phenyl)-4-(3-chlorophenyl)-5-(2-methylthio-pyrimidin-4-yl)-N—H-imidazole (F2.4)

To a solution of 2.30 g (4.3 mmol) F2.3 in 50 ml dry THF under nitrogen $LiAlH_4$ (1M in THF) was added at 0° C. until F2.3 could no longer be detected by HPLC. After hydrolysis with 0.4 ml water and removal of the solvent the residue was purified by column chromatography on basic ALOX (ethyl acetate) to yield 52% F2.4.
MS: M=507 (API+)

Example F3.1

2-(2,6-dichlorophenyl)-4-(4-chlorophenyl)-5-(2-methylthiopyrimidin-4-yl)-N—H-imidazole (F3.1)

An analogous reaction to that described in example F1.1, but starting with E3.1 gave F3.1 in 80% yield.
MS: M=449 (API+), 447 (API−)

Example F4.1

2-(2,6-dichlorophenyl)-4-(3-ethynylphenyl)-5-(2-methylthiopyrimidin-4-yl)-N—H-imidazole (F4.1)

An analogous reaction to that described in example F1.1, but starting with E4.1 gave F4.1 in 99% yield.
MS: M=437 (API+), 435 (API−)

Example F4.2

2-(2,6-dichloro-4-[methoxycarbonylmethoxy]phenyl)-4-(3-ethynylphenyl)-5-(2-methylthiopyrimidin-4-yl)-N—H-imidazole (F4.1)

An analogous reaction to that described in example F1.1, but starting with E4.2 gave F4.2 in quantitative yield.
MS: M=523 (ESI−)

Example F4.3

2-(2,6-dichloro-4-[2-hydroxyethoxy]phenyl)-4-(3-ethynylphenyl)-5-(2-methyl-thiopyrimidin-4-yl)-N—H-imidazole (F4.3)

An analogous reaction to that described in example F2.4, but starting with F4.2 gave F4.3 in 55% yield.
MS: M=495 (ESI−)

G Synthesis of the "N—H-imidazole sulfones"

Example G1.1

2-(2,6-dichlorophenyl)-4-(3-bromophenyl)-5-(2-methanesulfonylpyrimidin-4-yl)-N—H-imidazole (G1.1)

To a solution of 44.3 g (90.0 mmol) F1.1 in 2.15 l methanol was added a solution of 116.2 g (189 mmol) oxone™ in 1.7 l water. After stirring 5 hours at room temperature the methanol was distilled off an the residue taken up with ethyl acetate, washed with saturated aqueous sodium hydrogencarbonate, dried over sodium sulphate and evaporated to dryness. Chromatography of the residue on SiGel (n-heptane/ethyl acetate gradient 3:1 to 1:1) yielded 34.1 g (72%) G1.1, m.p. 231–233° C.
MS: M=525 (ESI+), M=523 (ESI−). $^1$H-NMR (250 MHz, CDCl$_3$): main tautomer (57%) δ=3.35 (s, 3H, CH$_3$), 7.3–7.7 (m, 6H, Ar—H), 7.84 (t, 1H, 2-H—Br-Ph), 8.64 (d, 1H, 6-H-pyrimidine), 11.2 (s, 1H, NH). $2^{nd}$ tautomer (43%) δ=2.92 (s, 3H, CH$_3$), 7.3–7.7 (m, 5H, Ar—H), 7.74 (t, 1H, 2-H—Br-Ph), 8.23 (d, 1H, 5-H-pyrimidine), 8.81 (d, 1H, 6-H-pyrimidine), 10.4 (s, 1H, NH).

Example G2.1

2-(2,6-dichlorophenyl)-4-(3-chlorophenyl)-5-(2-methanesulfonylpyrimidin-4-yl)-N—H-imidazole (G2.1)

An analogous reaction to that described in example G1.1, but starting with F2.1 gave G2.1 in 89% yield.
MS: M=481 (API+), 479 (API−)

Example G2.2

2-(2,6-dichloro-4-hydroxymethylphenyl)-4-(3-chlorophenyl)-5-(2-methane-sulfonyl-pyrimidin-4-yl)-N—H-imidazole (G2.2)

An analogous reaction to that described in example G1.1, but starting with F2.2 gave G2.2 in 62% yield.
MS: M=511 (API+), 509 (API−)

Example G2.3

2-(2,6-dichloro-4-[2-hydroxyethoxy]phenyl)-4-(3-chlorophenyl)-5-(2-methane-sulfonyl-pyrimidin-4-yl)-N—H-imidazole (G2.3)

An analogous reaction to that described in example G1.1, but starting with F2.4 gave G2.3 in 78% yield.
MS: M=539 (ESI−)

Example G3.1

2-(2,6-dichlorophenyl)-4-(4-chlorophenyl)-5-(2-methanesulfonylpyrimidin-4-yl)-N—H-imidazole (G3.1)

An analogous reaction to that described in example G1.1, but starting with F3.1 gave G3.1 in 87% yield.
MS: M=481 (API+), 479 (API−)

Example G4.1

2-(2,6-dichlorophenyl)-4-(3-ethynylphenyl)-5-(2-methanesulfonylpyrimidin-4-yl)-N—H-imidazole (G4.1)

An analogous reaction to that described in example G1.1, but starting with F4.1 gave G4.1 in 98% yield.
MS: M=469 (API+)

Example G4.2

2-(2,6-dichloro-4-[2-hydroxyethoxy]phenyl)-4-(3-ethynylphenyl)-5-(2-methane-sulfonylpyrimidin-4-yl)-N—H-imidazole (G4.2)

An analogous reaction to that described in example G1.1, but starting with F4.3 gave G4.2 in 65% yield.
MS: M=529 (ESI+), 527 (ESI−)

H Synthesis of the "N—H-imidazole phenylaminopyrimidines"

Example H1.1

2-(2,6-dichlorophenyl)-4-(3-bromophenyl)-5-(2-[4-(2-diethylamino-ethoxy)phenylamino]pyrimidin-4-yl)-N—H-imidazole (H1.1)

A solution of 117 mg (0.22 mmol) G1.1, 140 mg (0.67 mmol) 4-(2-diethylaminoethoxy)aniline and 60 µl (0.78 mmol) trifluoroacetic acid in 1.0 ml dry N-methylpyrrolidone was heated to 140° C. for 18 hours. Purification by preparative scale HPLC/MS on RP18 (methanol-water-gradient) yielded 39 mg (27%) of pure H1.1.
MS: M=653 (API+), 651 (API−)

Example H2.1.1

2-(2,6-dichlorophenyl)-4-(3-chlorophenyl)-5-(2-[4-(2-diethylamino-ethoxy)phenylamino]pyrimidin-4-yl)-N—H-imidazole (H2.1.1)

An analogous reaction to that described in example H1.1, but starting with G2.1 gave H2.1.1 in 51% yield.
MS: M=609 (API+), 607 (API−)

Example H2.1.2

2-(2,6-dichlorophenyl)-4-(3-chlorophenyl)-5-(2-[4-(2-hydroxyethoxy)phenyl-amino]pyrimidin-4-yl)-N—H-imidazole (H2.1.2)

An analogous reaction to that described in example H1.1, but starting with G2.1 and 4-(2-hydroxy-ethoxy)aniline gave H2.1.2 in 26% yield.
MS: M=554 (API+), 552 (API−)

Example H2.1.3

2-(2,6-dichlorophenyl)-4-(3-chlorophenyl)-5-(2-[4-dimethylaminophenyl-amino]pyrimidin-4-yl)-N—H-imidazole (H2.1.3)

An analogous reaction to that described in example H1.1, but starting with G2.1 and 4-dimethylamino-aniline gave H2.1.3 in 14% yield.
MS: M=537 (API+), 535 (API−)

Example H2.1.4

2-(2,6-dichlorophenyl)-4-(3-chlorophenyl)-5-(2-[4-morpholinophenyl-amino]pyrimidin-4-yl)-N—H-imidazole (H2.1.4)

An analogous reaction to that described in example H1.1, but starting with G2.1 and 4-morpholino-aniline gave H2.1.4 in 22% yield.
MS: M=579 (API+), 577 (API−)

Example H2.1.5

2-(2,6-dichlorophenyl)-4-(3-chlorophenyl)-5-(2-[4-(N-(2-hydroxyethyl)-sulfamoyl)phenylamino]-pyrimidin-4-yl)-N—H-imidazole (H2.1.5)

A solution of 150 mg (0.31 mmol) G2.1, 135 mg (0.62 mmol) 4-amino-N-(2-hydroxyethyl)benzene-sulfonamide and 156 µl (0.62 mmol) HCl in dioxane (4 M) in 0.2 ml N-methylpyrrolidone were heated under nitrogen to 100° C. for 17 hours. The reaction mixture was treated with water and $Na_2CO_3$ and extracted with ethyl acetate. Purification by column chromatography (silica, chloroform/methanol 95:5) yielded 6% H2.1.5 MS: M=617 (ESI+), 615 (ESI−)

Example H2.2.1

2-(2,6-dichloro-4-hydroxymethylphenyl)-4-(3-chlorophenyl)-5-(2-[4-(2-diethylaminoethoxy)-phenylamino]pyrimidin-4-yl)-N—H-imidazole (H2.2.1)

An analogous reaction to that described in example H1.1, but starting with G2.2 gave H2.2.1 in 30% yield.
MS: M=637 (API+), 635 (API−)

Example H2.2.2

2-(2,6-dichloro-4-hydroxymethylphenyl)-4-(3-chlorophenyl)-5-(2-[4-(2-hydroxyethoxy)-phenylamino]pyrimidin-4-yl)-N—H-imidazole (H2.2.2)

A solution of 50 mg (0.1 mmol) G2.2 and 23 mg (0.15 mmol) 4-(2-hydroxyethoxy)aniline in 0.1 ml dry N-methylpyrrolidone were heated under nitrogen for one day at 140° C. The reaction mixture was treated with water and extracted with ethyl acetate. Purification by preparative scale HPLC/MS on RP18 (methanol-water-gradient) yielded 5% of H2.2.2.
MS: M=580 (API−)

Example H2.3.1

2-(2,6-dichloro-4-[2-hydroxyethoxy]phenyl)-4-(3-chlorophenyl)-5-(2-[4-(2-diethylaminoethoxy)-phenylamino]pyrimidin-4-yl)-N—H-imidazole (H2.3.1)

An analogous reaction to that described in example H1.1, but starting with G2.3 gave H2.3.1 in 62% yield.
MS: M=669 (ESI+)

Example H2.3.2

2-(2,6-dichloro-4-[2-hydroxyethoxy]phenyl)-4-(3-chlorophenyl)-5-(2-[4-methylsufinyl-phenylamino]pyrimidin-4-yl)-N—H-imidazole (H2.3.2)

A solution of 80 mg (0.15 mmol) G2.3, 47 mg (0.3 mmol) 4-(methanesulfinyl)aniline and 152 µl (0.3 mmol) HCl in diethyl ether (2 M) in 0.1 ml dry N-methyl-pyrrolidone were heated under nitrogen at 140° C. overnight. The reaction mixture was treated with water, saturated aqueous $Na_2CO_3$ and extracted with ethyl acetate. Purification by column chromatography (silica, n-heptane/ethyl acetate gradient) yielded 6% of H2.3.2.
MS: M=618 (ESI+)

Example H2.3.3

2-(2,6-dichloro-4-[2-hydroxyethoxy]phenyl)-4-(3-chlorophenyl)-5-(2-[4-(N-(2-hydroxyethyl)-ulfamoyl)phenylamino]pyrimidin-4-yl)-N—H-imidazole (H2.3.3)

An analogous reaction to that described in example H2.1.5, but starting with G2.3 gave H2.3.3 in 4% yield.
MS: M=677 (ESI+), 675 (ESI−)

Example H3.1.1

2-(2,6-dichlorophenyl)-4-(4-chlorophenyl)-5-(2-[4-(2-diethylaminoethoxy)-phenylamino]pyrimidin-4-yl)-N—H-imidazole (H3.1.1)

An analogous reaction to that described in example H1.1, but starting with G3.1 gave H3.1.1 in 45% yield.

MS: M=609 (API+), 607 (API−)

Example H3.1.2

2-(2,6-dichlorophenyl)-4-(4-chlorophenyl)-5-(2-[4-morpholinophenyl-amino]pyrimidin-4-yl)-N—H-imidazole (H3.1.2)

An analogous reaction to that described in example H1.1, but starting with G3.1 and 4-morpholinoaniline gave H3.1.2 in 31% yield.

MS: M=579 (API+), 577 (API−)

Example H3.1.3

2-(2,6-dichlorophenyl)-4-(4-chlorophenyl)-5-(2-[4-hydroxyphenyl-amino]pyrimidin-4-yl)-N—H-imidazole (H3.1.3)

An analogous reaction to that described in example H1.1, but starting with G3.1 and 4-hydroxyaniline gave H3.1.3 in 59% yield.

MS: M=510 (API+), 508 (API−)

Example H3.1.4

2-(2,6-dichlorophenyl)-4-(4-chlorophenyl)-5-(2-[4-methoxyphenyl-amino]pyrimidin-4-yl)-N—H-imidazole (H3.1.4)

An analogous reaction to that described in example H1.1, but starting with G3.1 and 4-methoxyaniline gave H3.1.4 in 7% yield.

MS: M=524 (API+), 522 (API−)

Example H3.1.5

2-(2,6-dichlorophenyl)-4-(4-chlorophenyl)-5-(2-[4-ethoxyphenyl-amino]pyrimidin-4-yl)-N—H-imidazole (H3.1.5)

An analogous reaction to that described in example H1.1, but starting with G3.1 and 4-ethoxyaniline gave H3.1.5 in 34% yield

MS: M=538 (API+), 536 (API−)

Example H3.1.6

2-(2,6-dichlorophenyl)-4-(4-chlorophenyl)-5-(2-[4-pyridinylamino]pyrimidin-4-yl)-N—H-imidazole (H3.1.6)

An analogous reaction to that described in example H1.1, but starting with G3.1 and 4-aminopyridine and heating to 240° C. for 10 minutes in a microwave reactor gave H3.1.6 in 33% yield

MS: M=493 (API+)

Example H4.1.1

2-(2,6-dichlorophenyl)-4-(3-ethynylphenyl)-5-(2-[4-(2-diethylamino-ethoxy)phenylamino]pyrimidin-4-yl)-N—H-imidazole (H4.1.1)

An analogous reaction to that described in example H1.1, but starting with G4.1 gave H4.1.1 in 37% yield.

MS: M=597 (API+), 595 (API−)

Example H4.1.2

2-(2,6-dichlorophenyl)-4-(3-ethynylphenyl)-5-(2-[4-(2-hydroxyethoxy)-phenylamino]pyrimidin-4-yl)-N—H-imidazole (H4.1.2)

An analogous reaction to that described in example H1.1, but starting with G4.1 and 4-(2-hydroxy-ethoxy)aniline gave H4.1.2 in 29% yield.

MS: M=542 (API+), 540 (API−)

Example H4.2

2-(2,6-dichloro-4-[2-hydroxyethoxy]phenyl)-4-(3-ethynylphenyl)-5-(2-[4-(2-diethylaminoethoxy)-phenylamino]pyrimidin-4-yl)-N—H-imidazole (H4.2)

An analogous reaction to that described in example H1.1, but starting with G4.2 gave H4.2 in 23% yield.

MS: M=657 (ESI+)

LIST OF REFERENCES

Abounader, R., et al., J. Natl. Cancer Inst. 91 (1999) 1548–1556

Ansel, H., et. al., Pharmaceutical Dosage Forms and Drug Delivery Systems, 6th ed., (1995), pp. 196 and 1456–1457

Biscardi, J. S., et al., Adv. Cancer Res. 76 (2000) 61–119

Laterra, J., et al., Lab. Invest. 76 (1997) 565–577

Merrifield, Fed. Proc. Fed. Amer. Soc. Exp. Biol. 21 (1962) 412

Somei, M., and Tsuchiya, M., Chem. Pharm. Bull. 29 (1981) 3145–3157

Susva, M., et al., Trends Pharmacol. Sci. 21 (2000) 489–495

Tomioka, D., Cancer Res. 61 (2001) 7518–7524

Wang, R., et al., J. Cell Biol. 153 (2001) 1023–1033

WO 96/18626

What is claimed:

1. Compounds of formula (I):

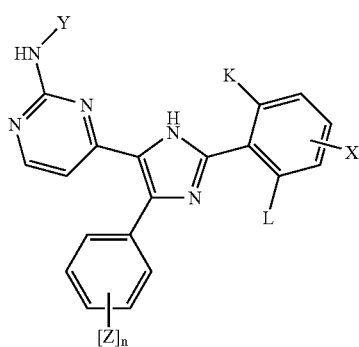

(I)

wherein:
K and L are selected from the group consisting of hydrogen; halogen; alkyl; —OH; and —O-alkyl;
X is selected from the group consisting of hydrogen; —OR$^1$; —SR$^2$; —S(O)R$^2$; —S(O)$_2$R$^2$; —CH$_2$—S—CH$_2$—C(O)$_2$—CH$_2$—CH$_3$; —CH$_2$—S—(CH$_2$)$_2$—OH and a group A$^1$-Q; wherein:
A$^1$ is a C$_1$–C$_3$-alkylene group; and Q is selected from the group consisting of —OR$^1$; —SR$^2$; —S(O)R$^2$; —S(O)$_2$R$^2$; —NR$^3$R$^4$; —NH—(CH$^2$)$_2$—NR$^3$R$^4$ and halogen;
R$^1$ is selected from the group consisting of hydrogen; alkyl; allyl; dimethylphosphonylmethyl; 2,3-epoxy-1-propyl; (R)-2,3-dihydroxy-1-propyl; (S)-2,3-dihydroxy-1-propyl; 1,3-dihydroxy-2-propyl; 3-hydroxy-2-hydroxymethyl-1-propyl; 2-methoxyethoxymethyl; 2,2-dimethyl-1,3-dioxolan-4-ylmethyl and a group A$^1$-Q$^1$;
Q$^1$ is selected from the group consisting of —O-alkyl; —CN; —C(O)$_2$H; —C(O)$_2$-alkyl; —C(O)—NR$^3$R$^4$; —S-alkyl; —S(O)-alkyl and —S(O)$_2$-alkyl; except that if A$^1$ represents 1,2-ethylen- or 1,3-propylene group then Q$^1$ is —OH or —NR$^3$R$^4$;
R$^3$ and R$^4$ are independently hydrogen or alkyl; or R$^3$ and R$^4$ together with the nitrogen atom to which they are attached form a 5 to 7 membered, saturated or unsaturated ring, which is unsubstituted or substituted by a methyl group and wherein one additional nitrogen- or oxygen atom is present, with the remaining atoms being carbon atoms;
R$^2$ is selected from the group consisting of alkyl; dimethylphosphonylmethyl; 2,3-epoxy-1-propyl; 2,3-dihydroxy-1-propyl; 2,2-dimethyl-1,3-dioxolan-4-ylmethyl and A$^1$-Q$^1$;
Y is aryl or heteroaryl, which are both unsubstituted or substituted one, two or three times by halogen;

—CH₂OR⁵; —R⁵; —OR⁵; —NR⁶R⁷; —SR⁵; —S(O)R⁵; —S(O)₂R⁵; —S(O)NHR⁵; —S(O)₂NHR⁵; —S(O)NR⁶R⁷; —S(O)₂NR⁶R⁷; —C(O)NHR⁵; —C(O)NR⁶R⁷; or CN;

wherein:
R⁵ is hydrogen or alkyl, which alkyl is unsubstituted or substituted with OH, —O-alkyl or —NR⁶R⁷, with the proviso that two heteroatoms are not connected to the same carbon atom;

R⁶ and R⁷ are independently hydrogen or alkyl; or R⁶ and R⁷ together with the nitrogen atom to which they are attached form a 5 to 7 membered, saturated or unsaturated ring, which is unsubstituted or substituted by a methyl group and wherein one additional nitrogen- or oxygen atom is present, with the remaining atoms being carbon atoms;

Z is selected from the group consisting of halogen; —OH; —O-allyl; alkyl; methoxymethoxy; (2-methoxyethoxy)methyloxy; methylthio; ethoxymethoxy; methylenedioxy; ethynyl; trimethylsilylethynyl; —O-alkyl, wherein the alkyl group is unsubstituted or substituted with pyridinyl; and benzyloxy which is unsubstituted or substituted by halogen, methoxy, ethoxy, methylenedioxy, —CN, —NO₂, or —C(O)₂H; and n is 1 or 2;

or pharmaceutically acceptable salts thereof.

2. The compounds of claim 1, wherein:
K and L are both chlorine;
X is hydrogen, alkyl or —O-alkyl; which alkyl groups are substituted by —OH; and
Y, Z and n are as defined in claim 1;
or pharmaceutically acceptable salts thereof.

3. The compounds of claim 2, wherein:
K and L are both chlorine;
X is hydrogen, alkyl or —O-alkyl; which alkyl groups are substituted by —OH;
Z is halogen or ethynyl;
Y is phenyl, which is unsubstituted or once substituted by halogen; —CH₂OR⁵; —R⁵; —OR⁵; —NR⁶R⁷; —SR⁵; —S(O)R⁵; —S(O)₂R⁵; —S(O)NHR⁵; —S(O)₂NHR⁵; —S(O)NR⁶R⁷; —S(O)₂NR⁶R⁷; —C(O)NHR⁵; —C(O)NR⁶R⁷; or CN;
R⁵ is hydrogen or alkyl which alkyl is unsubstituted or substituted with OH, —O-alkyl or —NR⁶R⁷, with the proviso that two heteroatoms are not connected to the same carbon atom;
R⁶ and R⁷ independently represent hydrogen or alkyl; and
n is 1;
or pharmaceutically acceptable salts thereof.

4. A compound selected from the group consisting of:
2-(2,6-dichlorophenyl)-4-(3-bromophenyl)-5-(2-[4-(2-diethylamino-ethoxy)phenylamino]pyrimidin-4-yl)-N—H-imidazole,
2-(2,6-dichlorophenyl)-4-(3-chlorophenyl)-5-(2-[4-(2-diethylamino-ethoxy)phenylamino]pyrimidin-4-yl)-N—H-imidazole,
2-(2,6-dichlorophenyl)-4-(3-chlorophenyl)-5-(2-[4-(2-hydroxyethoxy)phenyl-amino]pyrimidin-4-yl)-N—H-imidazole,
2-(2,6-dichlorophenyl)-4-(3-chlorophenyl)-5-(2-[4-dimethylaminophenyl-amino]pyrimidin-4-yl)-N—H-imidazole,
2-(2,6-dichlorophenyl)-4-(3-chlorophenyl)-5-(2-[4-(N-(2-hydroxyethyl)-sulfamoyl)phenylamino]-pyrimidin-4-yl)-N—H-imidazole,
2-(2,6-dichloro-4-hydroxymethylphenyl)-4-(3-chlorophenyl)-5-(2-[4-(2-diethylaminoethoxy)-phenylamino]pyrimidin-4-yl)-N—H-imidazole,
2-(2,6-dichloro-4-hydroxymethylphenyl)-4-(3-chlorophenyl)-5-(2-[4-(2-hydroxyethoxy)-phenylamino]pyrimidin-4-yl)-N—H-imidazole,
2-(2,6-dichloro-4-[2-hydroxyethoxy]phenyl)-4-(3-chlorophenyl)-5-(2-[4-(2-diethylaminoethoxy)-phenylamino]pyrimidin-4-yl)-N—H-imidazole,
2-(2,6-dichloro-4-[2-hydroxyethoxy]phenyl)-4-(3-chlorophenyl)-5-(2-[4-methylsufinyl-phenylamino]pyrimidin-4-yl)-N—H-imidazole,
2-(2,6-dichloro-4-[2-hydroxyethoxy]phenyl)-4-(3-chlorophenyl)-5-(2-[4-(N-(2-hydroxyethyl)-sulfamoyl)phenylamino]pyrimidin-4-yl)-N—H-imidazole,
2-(2,6-dichlorophenyl)-4-(4-chlorophenyl)-5-(2-[4-(2-diethylaminoethoxy)-phenylamino]pyrimidin-4-yl)-N—H-imidazole,
2-(2,6-dichlorophenyl)-4-(4-chlorophenyl)-5-(2-[4-hydroxyphenyl-amino]pyrimidin-4-yl)-N—H-imidazole,
2-(2,6-dichlorophenyl)-4-(4-chlorophenyl)-5-(2-[4-methoxyphenyl-amino]pyrimidin-4-yl)-N—H-imidazole,
2-(2,6-dichlorophenyl)-4-(4-chlorophenyl)-5-(2-[4-ethoxyphenyl-amino]pyrimidin-4-yl)-N—H-imidazole,
2-(2,6-dichlorophenyl)-4-(3-ethynylphenyl)-5-(2-[4-(2-diethylamino-ethoxy)phenylamino]pyrimidin-4-yl)-N—H-imidazole,
2-(2,6-dichlorophenyl)-4-(3-ethynylphenyl)-5-(2-[4-(2-hydroxyethoxy)-phenylamino]pyrimidin-4-yl)-N—H-imidazole, and
2-(2,6-dichloro-4-[2-hydroxyethoxy]phenyl)-4-(3-ethynylphenyl)-5-(2-[4-(2-diethylaminoethoxy)-phenylamino]pyrimidin-4-yl)-N—H-imidazole.

5. The compound of claim 2, wherein
K and L are both chlorine;
X is hydrogen;
Z is halogen;
Y is phenyl, which is substituted by —NR⁶R⁷, wherein R⁶ and R⁷ together with the nitrogen atom to which they are attached form a 5 to 7 membered, saturated or unsaturated ring, which is unsubstituted or substituted by a methyl group and wherein one additional nitrogen- or oxygen atom is present, with the remaining atoms being C-atoms; and
n is 1;
or pharmaceutically acceptable salts thereof.

6. A compound selected from the group consisting of:
2-(2,6-dichlorophenyl)-4-(4-chlorophenyl)-5-(2-[4-morpholinophenyl-amino]pyrimidin-4-yl)-N—H-imidazole, and
2-(2,6-dichlorophenyl)-4-(3-chlorophenyl)-5-(2-[4-morpholinophenyl-amino]pyrimidin-4-yl)-N—H-imidazole.

7. The compounds of claim 1, wherein:
K and L are both chlorine;
X is hydrogen;
Z is halogen;
Y is heteroaryl, which is unsubstituted or substituted one, two or three times by halogen; —CH₂OR⁵; —R⁵; —OR⁵; —NR⁶R⁷; —SR⁵; —S(O)R⁵; —S(O)₂R⁵; —S(O)NHR⁵; —S(O)₂NHR⁵; —S(O)NR⁶R⁷; —S(O)₂NR⁶R⁷; —C(O)NHR⁵; —C(O)NR⁶R⁷; or CN; wherein R⁵ is hydrogen or alkyl, which alkyl is unsubstituted or substituted with OH, —O-alkyl or —NR⁶R⁷, with the proviso that two heteroatoms are not connected to the same carbon atom;

R⁶ R⁷ independently represent hydrogen or alkyl; or R⁶ and R⁷ together with the nitrogen atom to which they are attached form a 5 to 7 membered, saturated or unsaturated ring, which is unsubstituted or substituted by a methyl group and wherein one additional nitrogen- or oxygen atom is present, with the remaining atoms being C-atoms; and n is 1; and or pharmaceutically acceptable salts thereof.

8. The compounds of claim 1, wherein:
K and L are both chlorine;
X is hydrogen;
Z is halogen;
Y is pyridinyl, which is unsubstituted or substituted by alkyl; and
n is 1;

or pharmaceutically acceptable salts thereof.

9. A compound of claim 1 wherein the compound is:
2-(2,6-dichlorophenyl)-4-(4-chlorophenyl)-5-(2-[4-pyridinylamino]-pyrimidin-4-yl)-N—H-imidazole.

10. A process for the production of a compound of the formula:

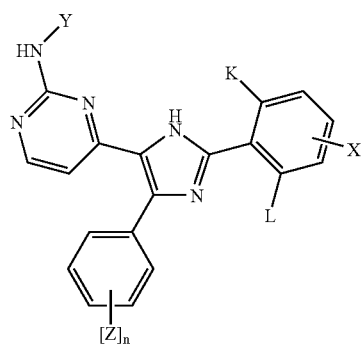

(I)

wherein:
K and L are selected from the group consisting of hydrogen; halogen; alkyl; —OH; and —O-alkyl;
X is selected from the group consisting of hydrogen; —OR¹; —SR²; —S(O)R²; —S(O)₂R²; —CH₂—S—CH₂—C(O)₂—CH₂—CH₃; —CH₂—S—(CH₂)₂—OH and a group A¹-Q; wherein:
A¹ is a C₁–C₃-alkylene group; and
Q is selected from the group consisting of —OR¹; —SR²; —S(O)R²; —S(O)₂R²; —NR³R⁴; —NH—(CH²)₂—NR³R⁴ and halogen;
R¹ is selected from the group consisting of hydrogen; alkyl; allyl; dimethylphosphonylmethyl; 2,3-epoxy-1-propyl; (R)-2,3-dihydroxy-1-propyl; (S)-2,3-dihydroxy-1-propyl; 1,3-dihydroxy-2-propyl; 3-hydroxy-2-hydroxymethyl-1-propyl; 2-methoxyethoxymethyl; 2,2-dimethyl-1,3-dioxolan-4-ylmethyl and a group A¹-Q¹;
Q¹ is selected from the group consisting of —O-alkyl; —CN; —C(O)₂H; —C(O)₂-alkyl; —C(O)—NR³R⁴; —S-alkyl; —S(O)-alkyl and —S(O)₂-alkyl; except that if A¹ represents A 1,2-ethylen- or 1,3-propylene group then Q¹ is —OH or —NR³R⁴;

R³ and R⁴ are independently hydrogen or alkyl; or R³ and R⁴ together with the nitrogen atom to which they are attached form a 5 to 7 membered, saturated or unsaturated ring, which is unsubstituted or substituted by a methyl group and wherein one additional nitrogen- or oxygen atom is present, with the remaining atoms being carbon atoms;

R² is selected from the group consisting of alkyl; dimethylphosphonylmethyl; 2,3-epoxy-1-propyl; 2,3-dihydroxy-1-propyl; 2,2-dimethyl-1,3-dioxolan-4-ylmethyl and A¹-Q¹;

Y is aryl or heteroaryl, which are both unsubstituted or substituted one, two or three times by halogen; —CH₂OR⁵; —R⁵; —OR⁵; —NR⁶R⁷; —SR⁵; —S(O)R⁵; —S(O)₂R⁵; —(S(O)NHR⁵; —S(O)₂NHR⁵; —S(O)NR⁶R⁷; —S(O)₂NR⁶R⁷; —C(O)NHR⁵; —C(O)NR⁶R⁷; or CN; wherein R⁵ is hydrogen or alkyl, which alkyl is unsubstituted or substituted with OH, —O-alkyl or —NR⁶R⁷, with the proviso that two heteroatoms are not connected to the same carbon atom;

R⁶ and R⁷ are independently hydrogen or alkyl; or R⁶ and R⁷ together with the nitrogen atom to which they are attached form a 5 to 7 membered, saturated or unsaturated ring, which is unsubstituted or substituted by a methyl group and wherein one additional nitrogen- or oxygen atom is present, with the remaining atoms being carbon atoms;

Z is selected from the group consisting of halogen; —OH; —O-allyl; alkyl; methoxymethoxy; (2-methoxyethoxy)methyloxy; methylthio; ethoxymethoxy; methylendioxy; ethynyl; trimethylsilylethynyl; —O-alkyl, wherein the alkyl group is unsubstituted or substituted with pyridinyl; and benzyloxy which is unsubstituted or substituted by halogen, methoxy, ethoxy, methylenedioxy, —CN, —NO₂, or —C(O)₂H; and n is 1 or 2;

or pharmaceutically acceptable salts thereof which comprises reacting a compound of the formula:

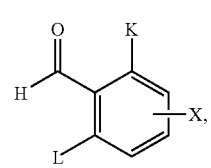

(II)

with a compound of the general formula:

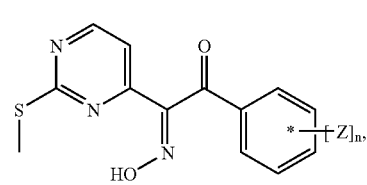

(III)

to obtain a compound of the formula:

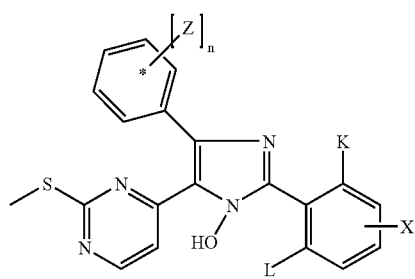

IV which thereafter undergoes N-deoxygenation to obtain a compound of the formula:

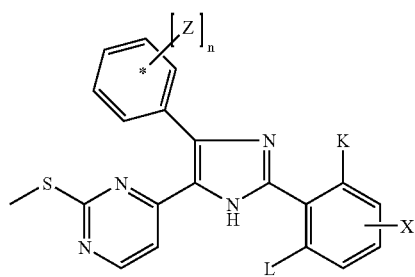

V which thereafter undergoes oxidation of the sulphide group to obtain a compound of the formula:

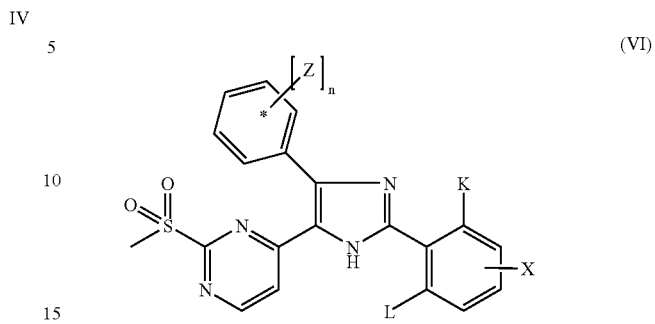

(VI)

which is reacted with a compound of the formula Y—NH$_2$ to give the compound of formula (I):

and isolating said compounds of formula (I) from the reaction mixture, and if desired turning them into a pharmaceutically acceptable salt by addition of suitable acids or bases.

11. A pharmaceutical composition comprising a compound of claim 1 together with pharmaceutically acceptable excipients.

12. A method of treating colon cancer comprising administering to a patient in need thereof a therapeutically effective amount of a compound of claim 1.

* * * * *

SEQUENCE LISTING

<160> NUMBER OF SEQ ID NOS: 2

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Glu Glu Glu Ile Tyr Gly Glu Phe Glu Ala Lys Lys Lys Lys
 1               5                  10                  15

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Aminocaprylic acid

<400> SEQUENCE: 2

Gly Xaa Ala Glu Glu Glu Ile Tyr Gly Glu Phe Glu Ala Lys Lys
 1               5                  10                  15

Lys